United States Patent [19]

Higuchi et al.

[11] Patent Number: 5,409,702
[45] Date of Patent: Apr. 25, 1995

[54] COSMETICS

[75] Inventors: Masako Higuchi, Neyagawa; Yasutaka Miura, Takatsuki; Yasuhiro Kinoshita; Yoshikazu Yamamoto, both of Neyagawa; Keisuke Tashiro, Shiga; Takashi Yoshii, Yasu, all of Japan

[73] Assignee: Nippon Paint Co., Ltd., Osaka, Japan

[21] Appl. No.: 109,018

[22] Filed: Aug. 18, 1993

Related U.S. Application Data

[63] Continuation of Ser. No. 848,434, Mar. 9, 1992, abandoned.

[30] Foreign Application Priority Data

Mar. 8, 1991 [JP] Japan ................................ 3-043487

[51] Int. Cl.⁶ ........................ A61K 35/78; C12P 39/00
[52] U.S. Cl. .................................... 424/195.1; 435/42
[58] Field of Search ........................ 435/42; 424/195.1

[56] References Cited

U.S. PATENT DOCUMENTS 4,536,474 8/1985 Yamamoto et al. .................. 435/42

FOREIGN PATENT DOCUMENTS

| 973553 | 2/1951 | France . | |
|---|---|---|---|
| 61-158912 | 7/1986 | Japan | A61K 7/00 |
| 1158912 | 7/1986 | Japan | A61K 7/00 |
| 3200708 | 2/1991 | Japan | A61K 7/00 |
| 4-282319 | 10/1992 | Japan | A61K 35/82 |
| 4-282320 | 10/1992 | Japan | A61K 35/82 |
| 2189505 | 10/1987 | United Kingdom | A01G 33/00 |

OTHER PUBLICATIONS

Inoue and Iwaida, "Usnic Acid Extracted from Lichens, and Its Utilization", *J. Soc. Cosmet. Chem. Japan,* vol. 14, (1), pp. 57–61, (1980).

*Primary Examiner*—Douglas W. Robinson
*Assistant Examiner*—Howard C. Lee
*Attorney, Agent, or Firm*—Townsend & Banta

[57] ABSTRACT

Stable and safe cosmetic compositions comprising melanin production inhibitors wherein the melanin production inhibitors have been extracted lichens cell cultures.

2 Claims, No Drawings

COSMETICS

This is a continuation of application Ser. No. 07/848,434, filed on Mar. 9, 1992, which was abandoned on Sep. 29, 1993.

TECHNICAL FIELD

The present invention relates to cosmetic compositions having excellent facial effects comprising lichen cultured cell extracts.

BACKGROUND OF THE INVENTION

Lichens are consortiums consisting of some kinds of fungi and algae and belong to a group of plants which occupy a botanically specific position. Metabolites of these lichens, that is, lichen components are quite different from components of other various higher or lower plants and they belong to a botanically specific class. They are definitely classified by Asahina et al. (See Asahina and Shibata, "Chemistry of Lichen Components," published by Kawade Shobo, 1948.)

It has been considered that a physiological significance of lichen components exists in defense against attack of microorganisms or insect plague because lichens grow slowly, or it exists in defense against ultraviolet rays because they grow in the sunshine, different from other fungi. Therefore, lichen components have hitherto been used for applications which came out of these functions. Examples thereof include dyes, antibiotics, flavors and the like. However, in fact, little study has been made on a pharmacological effect of these lichen components.

Lichens grow slowly and, further, their growth is liable to be restricted by natural environments (e.g. season, climate, temperature, latitude, etc.) as well as artificial environments (e.g. sulphur dioxide gas concentration, smoke concentration, etc.). Therefore, it is extremely difficult to culture lichens, which results in no success. Further, as is often the case in lichens, there the two are similar in form, but totally different in component. Therefore, selection of raw materials requires great skill and it is difficult to collect from nature. In order to obtain a method for producing lichen components, a study on cell culture has recently been made. Since lichens grow rapidly by cell culture in comparison with natural culture which needs a growth period of years or months. Therefore, it is possible to produce a subjective component in a short period of time. Further, different from a natural culture, there are advantages that it is not influenced by the weather and need not a lot of persons on collection and, further, it is possible to conduct planned production on an industrial scale. As a method comprising for culturing lichen cultured cells to be extracted and collecting a lichen component from the cells, for example, there is the present inventor's application (Japanese Patent application No. 58-56689); however, it was not known whether lichen cultured cells produce a melanin production inhibitor or not.

A melanin pigment which causes coloring of skin is produced at a melanin production granule in melanocyte between cutical and corium and melanin thus produced diffuses into adjacent cells. At present, a biochemical reaction in melanocyte is assumed to be as follows. One of essential amino acids, that is, tyrosine converts into dopa, further into dopaquinone due to an action of tyrosinase, which changes into black melanin through red pigment or colorless pigment due to enzymatic or nonenzymatic oxidation action. This process is a production process of melanin pigment. Accordingly, it is considered that production of melanin can be depressed by depressing biosynthesis of tyrosinase or depressing an action of tyrosinase as the first stage of the reaction, or by reducing quinones at an intermediate stage. Accordingly, facial effect can be obtained by formulating a substance which depresses biosynthesis of tyrosinase, or depresses or inhibits the action of tyrosinase.

It has been suggested that the certain substances produce the above mentioned depression. These include substances which bond with copper as an active center of tyrosinase (e.g. thiourea, cysteine, kojic acid, etc.) substances which can become a competitive substance with tyrosine as a substrate of tyrosinase (e.g. N-acetyltyrosine, $\gamma$-pyrone, hinokitiol, etc.), substances which elongate an induction period of the reaction of tyrosinase and substrate (e.g. Tween 20, etc.), substances which selectively bond with o-dihydroxy group such as dopa (e.g. molybdenum ion, etc.), substances which bond with o-quinones (e.g. aniline, etc.), reductants for o-quinones (e.g. acorbic acid, hydroquinone and derivatives thereof, etc.) and the like.

Cosmetics wherein such melanin production inhibitors are formulated, however, are not satisfactory in view of toxicity, stability and influence due to functional group for human. Accordingly, the development of cosmetics containing stable melanin production inhibitors in high safety has been requested heretofore.

Under these circumstances, the present inventors have paid attention to cosmetics wherein natural products are formulated in view of safety. Further, the present inventors have intensively studied whether extracts of lichens which have ever been used as a crude drug can be used as cosmetics having excellent facial effect or not. As a result, it has been found that the production inhibitors extracted from lichen cultures, and the present invention has been completed.

SUMMARY OF THE INVENTION

According to the present invention, it is possible to produce melanin production inhibitors extracted from lichen cultures. Safe and stable cosmetics compositions can be made with these melanin inhibitors. The cosmetics of the present invention can be in the form of various products such as cosmetic cream, milky lotion, beauty wash, packing agency, lipstick, under makeup, foundation, suncare and the like, particularly cosmetics for skin. These cosmetics having excellent facial effect during and after use.

In addition to the above, it is also disclosed the process for making the lichen cell culture extracts. Furthermore, methods of use are herein disclosed.

DESCRIPTION OF THE INVENTION

Under these circumstances, the present inventors have paid attention to cosmetics wherein natural products are formulated in view of safety. Further, the present inventors have intensively studied whether extracts of lichens which have ever been used as a crude drug can be used as cosmetics having excellent facial effect or not. As a result, it has been found that the above objects can be attained by formulating melanin production inhibitors extracted from lichen cultures, and the present invention has been completed.

That is, according to the present invention, there is provided cosmetics comprising one or more sorts of melanin production inhibitors extracted from cell cultures of lichens.

The lichen culture used in the present invention can be obtained by culturing lichens which belong to the following families. Examples thereof include Teloschistaceae, Physciaceae, Buelliaceae, Usneaceae, Anziaceae, Parmeliaceae, Canelariaceae, Lacanoraceae, Acarosporaceae, Gyrophoraceae, Cladoniaceae, Baeomycetacee, Stereocaulonaceae, Lecideaceae, Gyalectaceae, Asterothyriaceae, Stictaceae, Peltigeraceae, Pannariaceae, Coccocarpiaceae, Lecotheciaceae, Heppiaceae, Collemaceae, Lichinaceae, Graphidacea, Thelotremataceae, Diploschistacea, Verrucariaceae, Pyrenulaceae, Strigulaceae, Sphareophoraceae, Calciaceae, Cypheliaceae, Lecanactidaceae, OpegraDhaceae, Arthopyreniaceae, Arthoniaceae, Dictyonemataceae, Clavariaceae, Agaricaceae, and the like. Among them, substances having high melanin production inhibitory activity can be obtained from cultures of lichens which belong to the family Parmeliaceae, Usneaceae, Graphidaceae, Lecideaceae, Gyrophoraceae and Lecanoraceae, and they are preferred. The term "lichen culture" used herein means a culture of lichen cells, algae cells or indifferent symbiotic cultured tissue wherein both cells are present.

In order to prepare an extract for a melanin production inhibitor from lichen cultured cells, a lichen culture which has already been cultured is dipped in a solvent after freeze-drying. In view of safety of melanin production inhibitory activity, it is preferred that dipping is conducted at a low temperature (0° to 15° C.). The solvent for dipping may be any solvent such as water, polar organic solvent and non-polar organic solvent. Among them, polar solvents such as alcohol, ketone, ester and the like (particularly alcohol) are preferred in view of extraction efficiency.

After filtering a dipping solution, the resulting solvent after extraction was removed, typically by distillation, to obtain a substance having melanin production inhibitory activity.

One or more sorts of the above substances obtained from lichen cultures are mixed and the mixture is dissolved or dispersed in a cosmetically acceptable carrier; substrates which are often employed for cosmetics (e.g. fats and oils such as olive oil, mink oil; waxes such as lanolin, beeswax; hydrocarbons such as vaseline, squalene; esters such as isopropyl palmitate; higher alcohols such as cetyl alcohol, lauryl alcohol; higher fatty acids such as stearic acid, palmitic acid; sterols such as cholesterol, etc.) or alcohols (e.g. ethanol, isopropyl alcohol, propylene glycol, etc.) to obtain various cosmetics (e.g. cosmetic cream, milky lotion, pack, cleaning lotion, foundation, cheek rouge, lipstick, face powder, soap, shampoo, rinse, perfume, eau de cologne, etc.). In this case, various additives (e.g. surfactants, solvents, pigments, preservatives, antioxidants, humectants, vitamin, animal and plant extracts, etc.) can be used in combination.

Further, various cosmetics described above may take any form such as solution, emulsion, ointment, oil, wax, gel, sol, powder, spray and the like.

An amount of one or more sorts of substances thus obtained to be formulated in cosmetics can appropriately be selected or changed according to the form of use. In general, it may be an effective amount. It is preferred that the amount is 0.001 to 20% by weight, preferably 0.5 to 10% by weight based on the total weight of the cosmetic composition.

Analytical Methods

A. Test Method of Tyrosinase Inhibitory Activity Tyrosinase inhibitory activity was evaluated by the following method:

(1) Preparation of Reaction Solutions.

In the case of the measurement of tyrosinase activity, each reaction solution (No. 1 to No. 3 as described in Table 1) was prepared and each placed into a 1 ml. spectrophotometer cell.

TABLE 1

| Composition of reaction solution (ml) | | | |
|---|---|---|---|
| | No. 1 | No. 2 | No 3 |
| Buffer* | 0.50 | 0.50 | 0.50 |
| Substrate** | — | — | 0.20 |
| Inhibitor*** | — | — | 0.10 |
| Deionized water | 0.48 | 0.28 | 0.18 |

*0.1M phosphate-potassium (pH 6.8) solution
**2 μM L-dopa (manufactured by Wako Seiyaku K.K.)
***1% solution of lichen culture tyrosinase inhibitor prepared below (2) Measurement of tyrosinase activity About 0. 20 ml of 0.05% mg/ml Tyrosinase, manufactured by Sigma Co., is added to each cell. By using a spectrophotometer, change of an absorbance (471 nm) with time is measured 3 minutes after addition to each cell. Inhibition ratio (%) was calculated by an equation:

$$\{1-(Ab.3-Ab.1/Ab.2-Ab.1)\} \times 100$$

wherein Ab.2 is an absorbance of No.2, Ab.3 is an absorbance of No.3 at which Ab.2 becomes maximum and Ab.1 is an absorbance at which Ab.2 becomes maximum.

Preparation of lichen culture Tyrosinase inhibitors

An indifferent multiplicated tissue of *Parmelia entotheiochora* was freeze-dried and pulverized in a mortar, and 20 g of the resulting powder was dipped into 1000 ml of methanol for twenty-four hours. The mixture was filtered off and the solvent was removed by distillation resulting in an extract solution to obtain 2.5 g of an inhibitor. A methanol extract (10 mg) was dissolved in a small amount of methanol and diluted with a deionized water to obtain 1 ml of a solution (Reference Example 1) and a part of the solution (0.1 ml) was used for the test in method A above. As a result, tyrosinase inhibition ratio was 63%.

A second second lichen culture *Parmelia entotheichora* (Reference Example 2), along with other Tyrosinase inhibitors from various lichen were made according to the above process (Reference Examples 3-15) and are listed in the following table.

| | | Inhibitor (g) | Inhibition Ratio (%) |
|---|---|---|---|
| Ref. Example 3 | Cetraria juniperina | 1.5 | 65 |
| Ref. Example 4 | Usnea longissima | 2.5 | 44 |
| Ref. Example 5 | Ramalina vasudae | 2.2 | 54 |
| Ref. Example 6 | Graphis scripta | 1.8 | 46 |
| Ref. Example 7 | Graphis scripta | 2.3 | 38 |
| Ref. Example 8 | Phaeographis exaltata | 3.3 | 52 |

-continued

| | | Inhibitor (g) | Inhibition Ratio (%) |
|---|---|---|---|
| Ref. Example 9 | Lecidea adressula | 2.4 | 35 |
| Ref. Example 10 | Lecidea albocoeru- lescens | 1.8 | 41 |
| Ref. Example 11 | Rhizocarpon geogra- phicum | 1.9 | 44 |
| Ref. Example 12 | Umbilicaria caroli- niana | 2.1 | 45 |
| Ref. Example 13 | Lasallia pensylvanica | 1.2 | 52 |
| Ref. Example 14 | Haematomma ocrophaeum | 2.1 | 48 |
| Ref. Example 15 | Pertusaria flavicans | 2.1 | 49 |

B. Measurement of Melanin Production Inhibition Effect Tyrosinase synthesis inhibition and tyrosinase inhibition effect to melanocyte was evaluated using cultured pigment cells by the following method.

(1) Preparation of test culture medium 45 mls of an Eagle's MEM culture medium (containing no fetal bovine serum) was added to 1.25 ml of 1% lichens extract solution obtained as disclosed below. The mixture was filtered off using a filter having a pore size of 0.2 μm. 2 ml of fetal bovine serum was added to the filtrate to obtain a test culture medium.

(2) Test method 4 ml of a test culture medium (4 ml) was placed in a petri dish having a diameter of 6 cm and culture medium pigment cells (B-16 melanoma, $1 \times 10^5/0.2$ ml) were added. This was incubated at 37° C. for 6 days under a mixed environment (5% carbon dioxide/air) and the test medium was changed after 4 days. After 6 days, 0.025% trypsin/0.01% EDTA mixed solution was added to float cells. Then, pigment cells were collected by centrifugation at 700 rpm for 10 minutes and the amount of melanin produced was measured by a spectrophotometer (660 nm). By using the amount of melanin produced by culturing which contains no lichens extracts as a no addition control, melanin production inhibition ratio was determined.

Melanin production inhibition ratio (%) =

$$1 - \frac{\text{Amount of melanin produced in test cultured cells}}{\text{Amount of melanin produced in no addition control}} \times 100 \, (\%)$$

Lichen extract

About 20 mg of Reference Example 2 was dissolved in an extremely small amount of ethanol and diluted with a deionized water to obtain about 2 mls of a solution of which 1.25 ml was used for a test in Analytical Method B. As a result, melanin production inhibition ratio was 76% (Reference Example 2).

Practical Examples

EXAMPLE 1

| Cosmetic Cream | |
|---|---|
| Component | Amount (% by weight) |
| Inhibitor of Ref. Example 2 | 5.0 |
| Beeswax | 2.0 |
| Stearyl alcohol | 5.0 |
| Stearic acid | 8.0 |

| Cosmetic Cream | |
|---|---|
| Component | Amount (% by weight) |
| Squalene | 10.0 |
| Glyceryl monostearate | 3.0 |
| Polyoxyethylene stearate | 1.0 |
| Propylene glycol | 5.0 |
| Potassium hydroxide | 3.0 |
| Purified water containing suitable amounts of preservative, antioxidant and flavoring | up to 100% |

EXAMPLE 2

Cosmetic Cream

A formulation is the same as that Example 1 except for changing Ref. Example 2 Ref. Example 9.

EXAMPLE 3

| Milky Lotion | |
|---|---|
| Component | Amount (% by weight) |
| Inhibitor of Ref. Example 3 | 2.5 |
| Inhibitor of Ref. Example 4 | 2.5 |
| Squalene | 8.0 |
| Petrolatum* | 2.0 |
| Beeswax | 0.5 |
| Sorbitan sesquioleate | 0.8 |
| Polyoxyethylene oleyl ether | 1.2 |
| Carboxyvinyl polymer | 0.2 |
| Propylene glycol | 5.0 |
| Potassium hydroxide | 0.1 |
| Ethanol | 7.0 |
| Purified water containing suitable amounts of preservative, antioxidant and flavoring | up to 100% |

*Vaseline, available from Cheseborough Ponds, Inc.

EXAMPLE 4

Milky Lotion

A formulation is the same as that of Example 3 except for changing Ref. Examples 3 and 4 of Example 3 to Ref. Examples 10 and 11.

EXAMPLE 5

| Cosmetic Cream | |
|---|---|
| Component | Amount (% by weight) |
| Inhibitor of Ref. Example 5 | 2.5 |
| Inhibitor of Ref. Example 6 | 2.5 |
| Glycerin | 5.0 |
| Polyoxyethylene oleyl ether | 1.5 |
| Ethanol | 10.0 |
| Purified water containing suitable amounts of preservative, antioxidant, pigments and flavoring | up to 100% |

EXAMPLE 6

Cosmetic Cream

A formulation is the same as that of Example 5 except for changing Ref. Examples 5 and 6 to Ref. Examples 12 and 13.

EXAMPLE 7

| Packing Agent | |
|---|---|
| Component | Amount (% by weight) |
| Inhibitor of Ref. Example 7 | 2.5 |
| Inhibitor of Ref. Example 8 | 2.5 |
| Vinyl acetate emulsion | 15.0 |
| Polyvinyl alcohol | 10.0 |
| Olive oil | 3.9 |
| Glycerin | 5.0 |
| Titanium oxide | 8.0 |
| Kaolin | 7.0 |
| Ethanol | 5.0 |
| Purified water containing suitable amounts of preservative, antioxidant and flavoring | up to 100% |

EXAMPLE 8

Packing Agent

A formulation is the same as that of Example 7 except for changing Ref. Examples 7 and 8 to Ref. Examples 14 and 15.

We claim:

1. A method for inhibiting the production of melanin comprising applying to pigmented skin a melanin inhibiting amount of a melanin production inhibitor including a lichen cell culture extract of a polar solvent extract of a pulverized, freeze-dried lichen cell culture.

2. The method for inhibiting the production of melanin according to claim 1, further comprising preparing the lichen cell culture extract from a lichen cell culture selected from the group consisting of Parmelia, Usnea, Graphis, Lecidea, Gyrophora, Lecanora and mixtures thereof.

* * * * *